(12) United States Patent
Parker

(10) Patent No.: US 7,038,062 B2
(45) Date of Patent: May 2, 2006

(54) SYNTHESIS OF CYCLIC TRITHIOCARBONATES FROM EPOXIDES

(75) Inventor: Dane Kenton Parker, Massillon, OH (US)

(73) Assignee: The Goodyear Tire & Rubber Company, Akron, OH (US)

(*) Notice: Subject to any disclaimer, the term of this patent is extended or adjusted under 35 U.S.C. 154(b) by 110 days.

(21) Appl. No.: 10/882,824

(22) Filed: Jul. 1, 2004

(65) Prior Publication Data

US 2006/0004210 A1    Jan. 5, 2006

(51) Int. Cl.
*C07D 339/02*    (2006.01)

(52) U.S. Cl. ..................................................... 549/36
(58) Field of Classification Search ............... 549/36
See application file for complete search history.

(56) References Cited

U.S. PATENT DOCUMENTS

| | | | | |
|---|---|---|---|---|
| 3,073,846 | A | 1/1963 | Millikan et al. | 260/327 |
| 4,760,078 | A * | 7/1988 | Yamamoto et al. | 514/441 |
| 4,868,322 | A | 9/1989 | Degani et al. | 558/243 |
| 5,631,277 | A * | 5/1997 | Romer et al. | 514/441 |
| 5,817,837 | A * | 10/1998 | Muller et al. | 549/39 |

OTHER PUBLICATIONS

M Sander, Chem. Rev., 66, 297 (1966)).
Y. Taguchi et. al., Bull. Chem. Soc. Jpn., 60, 727 (1987).
J S Yadav et.al., JOC, 68, 2525 (2003)).
J Huddleston et al, Green Chem., 4, 156 (2001).

* cited by examiner

Primary Examiner—Deborah C. Lambkin
(74) Attorney, Agent, or Firm—Alvin T. Rockhill

(57) ABSTRACT

This invention provides a low cost technique for synthesizing cyclic trithiocarbonates by a simple one step process from epoxides that can be conducted under atmospheric pressure. This synthesis can be depicted as follows:

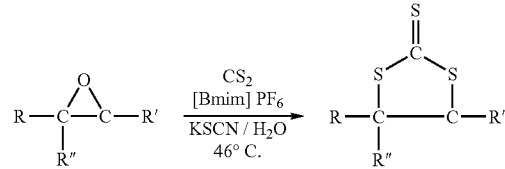

wherein R represents a moiety selected from the group consisting of alkyl groups and aryl groups, wherein R' represents a moiety selected from the group consisting of alkyl groups, aryl groups, and hydrogen atoms, and wherein R" represents a moiety selected from the group consisting of alkyl groups, aryl groups, and hydrogen atoms, wherein the R moiety and the R' moiety can be bonded together to form a cyclic structure, with the proviso that R" represents a hydrogen atom if R' represents an alkyl group or an aryl group. In this process carbon disulfide and a thiocyanate salt, such as potassium thiocyanate, are reacted with the epoxide in an ionic liquid, such as 1-butyl-3-methylimidazolium hexafluorophosphate ([Bmim] $PF_6$) in the presence of water to produce the cyclic trithiocarbonate.

20 Claims, No Drawings

SYNTHESIS OF CYCLIC TRITHIOCARBONATES FROM EPOXIDES

BACKGROUND OF THE INVENTION

Trithiocarbonates are of commercial importance in a wide variety of applications. For instance, trithiocarbonates are used a catalysts for the preparation of dihydric phenols, in pharmaceuticals, in rubber stabilization, as ore flotation agents, as chemical intermediates, and in rapid cure adhesives. In addition to these known applications, many trithiocarbonates have proven to be of exceptional utility as control agents for free radical polymerizations.

Although there are many techniques for the preparation of both symmetrical and unsymmetrical acyclic trithiocarbonates by nucleophilic substitution (see U.S. Pat. No. 4,868, 322), there are relatively few methods available for the preparation of substituted cyclic trithiocarbonate derivatives. In general, the analogous nucleophilic reactions depend on the use of 1,2-dihaloethane precursors. While useful for 1,2-dichlorethane itself, substituted derivatives such as 1-phenyl-1,2-dibromoethane are very prone to a dehydrohalogenation side reaction under the basic conditions commonly employed. This leads to low yields of the desired cyclic trithiocarbonates. More attractive as a general method for these substituted cyclic trithiocarbonates is the direct insertion of carbon disulfide into a thiirane (episulfide). While conceptually very simple, a review of the literature indicates several problems. First of all, the high reactivity and disagreeable odor of thiiranes are obstacles to the direct synthesis and use of these compounds (see M Sander, Chem. Rev., 66, 297 (1966)). Secondly, it is reported in both the patent (see U.S. Pat. No. 3,073,846) and published literature (see Y. Taguchi et. al., Bull. Chem. Soc. Jpn., 60, 727 (1987)), that the direct reaction of carbon disulfide with thiiranes requires high pressures, temperatures of 40° C. to 120° C. and "onium" or tertiary amine catalysts to obtain high yields. Needless to say, both these reaction features make this direct approach to cyclic trithiocarbonates onerous.

A recent article (J S Yadav et. al., JOC, 68, 2525 (2003)), describes the use of the hydrophobic ionic liquid [Bmim] PF6 as a novel and recyclable "solvent" for the conversion of oxiranes (epoxides) to thiiranes in an aqueous media in high yields at room temperature. This reaction can be depicted as follows:

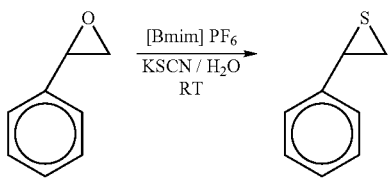

This reaction for phenyl thiirane is virtually quantitative. The reaction is also quite general for a wide variety of epoxides. Additionally, according to Yadev et. al., there are no examples in the literature on the use of ionic liquids for the conversion of epoxides to thiiranes.

SUMMARY OF THE INVENTION

This invention provides a low cost technique for synthesizing cyclic trithiocarbonates by a simple one step process that can be conducted under atmospheric pressure. This synthesis can be depicted as follows:

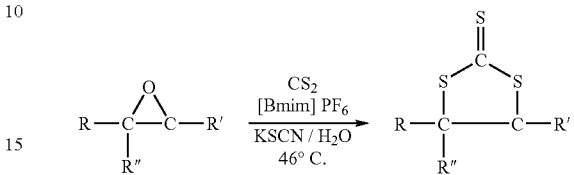

wherein R represents a moiety selected from the group consisting of alkyl groups and aryl groups, wherein R' represents a moiety selected from the group consisting of alkyl groups, aryl groups, and hydrogen atoms, and wherein R" represents a moiety selected from the group consisting of alkyl groups, aryl groups, and hydrogen atoms, wherein the R moiety and the R' moiety can be bonded together to form a cyclic structure, with the proviso that R" represents a hydrogen atom if R' represents an alkyl group or an aryl group. In this process carbon disulfide and a thiocyanate salt, such as potassium thiocyanate, are reacted with the epoxide in an ionic liquid, such as 1-butyl-3-methylimidazolium hexafluorophosphate ([Bmim] $PF_6$) in the presence of water to produce the cyclic trithiocarbonate.

The present invention more specifically relates to a process for synthesizing a cyclic trithiocarbonate which comprises reacting an epoxide with (1) a thiocyanate salt and (2) carbon disulfide, wherein said reaction is conducted in an ionic liquid in the presence of water at a temperature which is within the range of about −5° C. to about 200° C.

The present invention further reveals a process for synthesizing a cyclic trithiocarbonate of the structural formula:

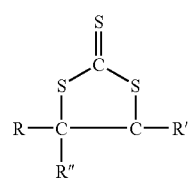

wherein R represents a moiety selected from the group consisting of alkyl groups and aryl groups, wherein R' represents a moiety selected from the group consisting of alkyl groups, aryl groups, and hydrogen atoms, and wherein R" represents a moiety selected from the group consisting of alkyl groups, aryl groups, and hydrogen atoms, wherein the R moiety and the R' moiety can be bonded together to form a cyclic structure, with the proviso that R" represents a hydrogen atom if R' represents an alkyl group or an aryl group, said process being comprised of reacting an epoxide with (1) a thiocyanate salt and (2) carbon disulfide, wherein the epoxide is of the structural formula:

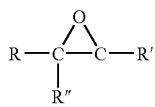

wherein R represents a moiety selected from the group consisting of alkyl groups and aryl groups, wherein R' represents a moiety selected from the group consisting of alkyl groups, aryl groups, and hydrogen atoms, and wherein R" represents a moiety selected from the group consisting of alkyl groups, aryl groups, and hydrogen atoms, wherein the R moiety and the R' moiety can be bonded together to form a cyclic structure, with the proviso that R" represents a hydrogen atom if R' represents an alkyl group or an aryl group, and wherein said reaction is conducted in an ionic liquid in the presence of water at a temperature which is within the range of about −5° C. to about 200° C.

DETAILED DESCRIPTION OF THE INVENTION

The epoxides that can be converted to cyclic thrthiocarbonates by utilizing the technique of this invention include monofunctionalized epoxides, difunctionalized epoxides, and trifunctionalized epoxides. The monofunctionalized epoxides that can be used are of the structural formula:

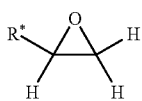

the difunctionalized epoxides that can be used are of the structural formula:

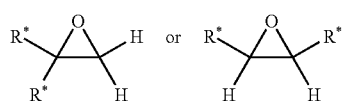

and the the trifunctionalized epoxides that can be used are of the structural formula:

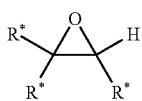

wherein R* represents a hydrocarbyl group or a functionalized hydrocarbyl group (including heterocyclic groups). The epoxide can also contain multiple epoxy groups, as shown in the following structures:

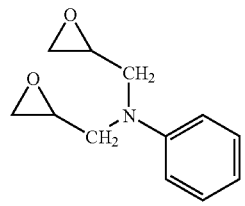

N,N-diglycidylaniline

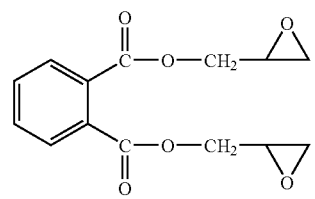

diglycidyl 1,2-cyclohexanedicarboxylate

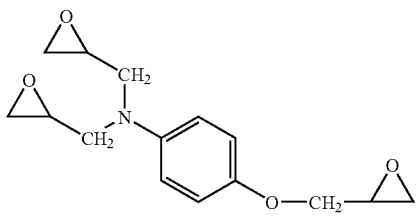

N,N-diglycidyl-4glycidyloxyaniline

Some other commercially available epoxides that can be used include 1,2-epoxy-5-hexane, 1,2-epoxy-3-methylbutane, 1,2-epoxy-2-methylpropane, 1,2-epoxy-7-octene, 1,2-epoxypentane, 1,2-epoxy-3-phenoxypropane, 3,4-epoxy-2-phenyl-1,1,1-trifluoro-2-butanol, (2,3-epoxypropyl)benzene, N-(2,3-epoxypropyl)phthalimide, 3,4-epoxytetrahydrothiophene-1,1-dioxide, glycerol diglycidyl ether, glycerol propoxylate triglycidyl ether, 3-glycidoxypropyldimethoxymethylsilane, 3-glycidoxypropyldimethethoxysilane, (glycidoxypropyldimethylsilyloxy)hepatcyclopentylpentacyclooctasiloxane, 3-glycidoxypropyltrimethoxysilane, (R)-(-)gylcidyl butyrate, glycidyl 2,2,3,3,4,4,5,5,6,6,7,7-dodecafluoroheptyl ether, glycidyl 2,2,3,3,4,4,5,5,6,6,7,7,8,8,9,9-hexadecafluorononyl ether, glycidyl isopropyl ether, glycidyl methacrylate, glycidyl 4-methoxyphenyl ether, (R)-(-)-glycidyl methyl ether, (S)-(-)-glycidyl methyl ether, and (2R)-(-)-glycidyl 3-nitrobenzenesulfonate.

The epoxides utilized in the practice of this invention will frequently be of the structural formula:

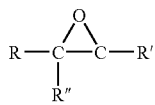

wherein R represents a moiety selected from the group consisting of alkyl groups and aryl groups, wherein R' represents a moiety selected from the group consisting of alkyl groups, aryl groups, and hydrogen atoms, and wherein R" represents a moiety selected from the group consisting of alkyl groups, aryl groups, and hydrogen atoms, wherein the R moiety and the R' moiety can be bonded together to form a cyclic structure, with the proviso that R" represents a hydrogen atom if R' represents an alkyl group or an aryl group. In many cases, R will represent an aryl group or an alkyl group containing from 1 to about 12 carbon atoms, and R' and R" will both represent hydrogen atoms. For instance R' and R" can both represent hydrogen atoms with R representing a phenyl group, a naphthyl group, an indenyl group, an anthracyl group, a phenanthryl group, a methyl group, an ethyl group, a normal propyl group, an isopropyl group, a normal butyl group, an isobutyl group, a tertiary butyl group, and the like.

R and R' can be alkyl moieties or aryl moieties which can be joined to form a cyclic structure. For instance, the epoxide can cyclohexeneoxide which can be converted to a cyclic trithiocarbonate according to the following reaction:

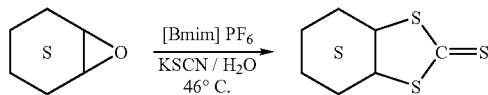

wherein Bmim PF$_6$ represents 1-butyl-3-methylimidazolium hexafluorophosphate.

The thiocyanate salt used will typically be a Group Ia metal salt or an ammonium salt. The thiocyanate salt will most typically be ammonium thiocyanate, sodium thiocyanate or potassium thiocyanate.

It is important for the ionic liquid employed to be in the liquid state at the reaction temperature used. The ionic liquid will accordingly have a melting point of less than about 100° C. The ionic liquid will typically have a melting point of less than 50° C. and will preferably be a liquid at room temperature (has a melting point of less than about 20° C.). This is achieved by incorporating a bulky asymmetric cation into the structure of the ionic liquid to prevent the ions from packing together easily. Salts based upon poor nucleophilic anions, such as $[BF_4]^-$, $[PF_3]^-$, $[CF_3CO_2]^-$, $CF_3SO_3]^-$, and $[Tf_2N]^-$, are water and air insensitive and also offer high thermal stability. Ambient temperature ionic liquids normally consist of a heterocyclic cation based upon a substituted imidazole or pyridine. A highly preferred cation is 1-butyl-3-methylimidazolium hexafluorophosphate which has the following structural formula:

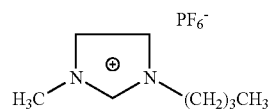

The synthesis of 1-butyl-3-methylimidazolim hexafluorophosphate is described by Jonathan G. Huddleston et al., "Characterization and Comparison of Hydrophilic and Hydrophobic Room Temperature Ionic Liquids Incorporating the Imidazolium Cation," Green Chemistry, 2001, Volume 3, at pages 156–164. The teachings of this reference are incorporated herein by reference in their entirety.

The carbon disulfide will be employed in an amount that is at least stoichiometric to the level of epoxide provided for the reaction. In most cases the carbon disulfide will be employed in a great excess to the stoichiometric amount. For instance, the carbon disulfide can be used in an amount where it serves in part as the reaction medium. The thiocyanate salt will be used at a level with is stoichiometric with the amount of epoxide provided for the reaction. The thiocyanate will typically be dissolved in a small amount of water.

The reaction will typically be conducted at a temperature which is within the range of about −5° C. to about 200° C. and will more typically be conducted at a temperature which is within the range of 10° C. to about 100° C. The reaction will preferably be conducted at a temperature which is within the range of about 20° C. (room temperature) to about 46° C. (the reflux temperature of carbon disulfide).

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLE 1

In this experiment styrene oxide which is readily available at low cost was convert to 4-phenyl-1,3-dithiolane-2-thione by utilizing the process of this invention. The reaction was carried out as a one step process which can be depicted as follows:

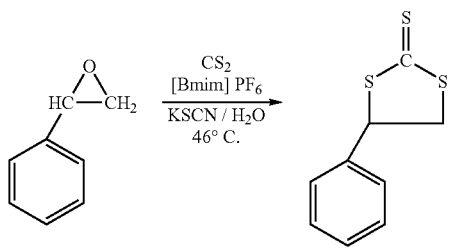

In the procedure used in this experiment a 500 ml 3-neck round bottom flask equipped with a magnetic stir bar, nitrogen inlet, pot thermometer, condenser and heating mantle was charged with 100 grams of ionic liquid (1-butyl-3-methylimidazolium hexafluorophosphate), 24.0 grams (0.20 moles) of styrene oxide, 20.0 grams (~0.20 moles) of potassium thiocyanate (KSCN), 25.0 grams of water, and 60 grams (0.79 moles) of carbon disulfide. The system was flushed with a slow purge of nitrogen and warmed to a temperature of about 30–35° C. At this point, a slow exotherm began to build and the color of the solution rapidly becames red-orange. The tempertaure of the reaction mixture was held at about 46° C. (the carbon disulfide reflux temperature) overnight. Then, 150 ml of water and 150 ml of carbon disulfide were added after about 18 hours with vigorous stirring to dissolve excess salts and extract the product from the ionic liquid. The mixture was subsequently placed in a separatory funnel. On standing, a clean 3 liquid phase separation took place with the water layer (pale yellow) on top, a clear orange carbon disulfide phase in the middle, and a darker orange ionic liquid phase on the bottom. The ionic liquid phase was separated and washed with 50 ml portions of carbon disulfide two times. The carbon disulfide phases were combined and evaporated to obtain about 40 grams of a bright yellow solid. Recrystallization of this material from 400 ml of a 1:3 acetone/hexane mixture gave 24.8 grams of a bright yellow crystalline solid having a melting point of 85–87° C. (the literature reports the melting point of 4-phenyl-1,3-dithiolane-2-thione to be 84–87° C.). From proton NMR, the material was determined to be about 99% pure. C13-NMR shows the distinctive trithiocarbonate carbon atom at 228.1 ppm.

EXAMPLE 2

The recycled ionic liquid from Example 1 (about 96 grams) was recharged to the reaction vessel as before with the identical amounts of the other reagents. The reaction was otherwise run in an identical manner to the procedure used in Example 1. After isolation and recrystalliztion 20.6 grams of the product were recovered.

EXAMPLE 3

The recycled ionic liquid from Example 2 was recharged into the reaction vessel as before with the identical amounts of the other reagents. The reaction was run in an identical manner to the procedure used in Example 1 and Example 2. After isolation and recrystalliztion 24.8 grams of the product were recovered. The recovered filtrate was reduced by about 50% in volume to recover a second crop of crystalline product (20 grams).

In total, about 88.6 grams (0.418 moles) of recrystallized product was obtained from 0.60 moles of styrene oxide which represents a yield of 69.7%. After the three cycles a total of 84.5 grams of the ionic liquid was recovered. Losses of the ionic liquid probably represent typical handling losses when working at this scale.

EXAMPLE 4

In this experiment 4-(n-butyl)-1,3-dithiolane-2-thione was synthesized by using the general procedure described in Example 1 with 1,2-epoxyhexane being substituted for the styrene oxide used in Example 1. This reaction can be depicted as follows:

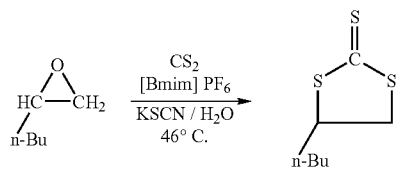

In the procedure used in this experiment a 50 ml 1-neck flask equipped with a magnetic stir bar, nitrogen inlet, pot thermometer, condenser and heating mantle was charged with 6 grams of ionic liquid (1-butyl-3-methylimidazolium hexafluorophosphate), 2.0 grams (0.02 moles) of 1,2-epoxy hexane, 2.0 grams (~0.02 moles) of potassium thiocyanate (KSCN), 2.5 grams of water, and 6 grams (0.079 moles) of carbon disulfide. The system was flushed with a slow purge of nitrogen and warmed to a temperature of about 30–35° C. At this point, a slow exotherm began to build and the color of the solution rapidly becames red-orange. The tempertaure of the reaction mixture was held at about 46° C. (the carbon disulfide reflux temperature) overnight. Then, 10 ml of water and 10 ml of carbon disulfide were added after about 18 hours with vigorous stirring to dissolve excess salts and extract the product from the ionic liquid. The mixture was subsequently placed in a separatory funnel. On standing, a clean 3 liquid phase separation took place with the water layer (pale yellow) on top, a clear orange carbon disulfide phase in the middle, and a darker orange ionic liquid phase on the bottom. The ionic liquid phase was separated and washed with 20 ml portions of carbon disulfide two times. The carbon disulfide phases were combined and evaporated to obtain about 3.22 grams of a bright yellow solid. Recrystallization of this material from 50 ml of a 1:3 acetone/hexane mixture gave 2.85 grams of product which represents a yield of about 89%.

EXAMPLE 5

In this experiment the procedure utilized in Example 4 was repeated except that cyclohexeneoxide (epoxycyclohexane) was substituted for the 1,2-epoxyhexane used in Example 1. The reaction employed in this experiment can be depicted as follows:

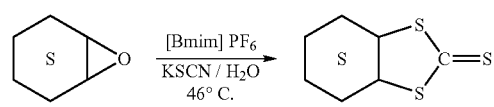

In this experiment 1.54 grams of yellow product having a melting point of 162–166° C. was recovered. This represents a yield of about 40% after the recrystalization.

While certain representative embodiments and details have been shown for the purpose of illustrating the subject invention, it will be apparent to those skilled in this art that various changes and modifications can be made therein without departing from the scope of the subject invention.

What is claimed is:
1. A process for synthesizing a cyclic trithiocarbonate which comprises reacting an epoxide with (1) a thiocyanate salt and (2) carbon disulfide, wherein said reaction is conducted in an ionic liquid in the presence of water at a temperature which is within the range of about −5° C. to about 200° C.

2. A process for synthesizing a cyclic trithiocarbonate of the structural formula:

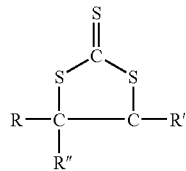

wherein R represents a moiety selected from the group consisting of alkyl groups and aryl groups, wherein R' represents a moiety selected from the group consisting of alkyl groups, aryl groups, and hydrogen atoms, and wherein R" represents a moiety selected from the group consisting of alkyl groups, aryl groups, and hydrogen atoms, wherein the R moiety and the R' moiety can be bonded together to form a cyclic structure, with the proviso that R" represents a hydrogen atom if R' represents an alkyl group or an aryl group, said process being comprised of reacting an epoxide with (1) a thiocyanate salt and (2) carbon disulfide, wherein the epoxide is of the structural formula:

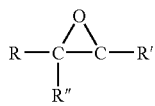

wherein R represents a moiety selected from the group consisting of alkyl groups and aryl groups, wherein R' represents a moiety selected from the group consisting of alkyl groups, aryl groups, and hydrogen atoms, and wherein R" represents a moiety selected from the group consisting of alkyl groups, aryl groups, and hydrogen atoms, wherein the R moiety and the R' moiety can be bonded together to form a cyclic structure, with the proviso that R" represents a hydrogen atom if R' represents an alkyl group or an aryl group, and wherein said reaction is conducted in an ionic liquid in the presence of water at a temperature which is within the range of about −5° C. to about 200° C.

3. A process as specified in claim 2 wherein R represents an alkyl group, wherein R' represents a hydrogen atom, and wherein R" represents a hydrogen atom.

4. A process as specified in claim 2 wherein R represents an aryl group wherein R' represents a hydrogen atom, and wherein R" represents a hydrogen atom.

5. A process as specified in claim 4 wherein the aryl group is a phenyl group.

6. A process as specified in claim 2 wherein the thiocyanate salt is selected from the group consisting of ammonium thiocyanate, sodium thiocyanate, and potassium thiocyanate.

7. A process as specified in claim 2 wherein said process is conducted at a temperature which is within the range of −5° C. to 200° C.

8. A process as specified in claim 2 wherein said process is conducted at a temperature which is within the range of 10° C. to 100° C.

9. A process as specified in claim 2 wherein said process is conducted at a temperature which is within the range of about 20° C. to about 46° C.

10. A process as specified in claim 2 wherein the ionic liquid is a hydrophobic alkylated imidazolium hexafluorophosphate salt.

11. A process as specified in claim 2 wherein the ionic liquid is 1-butyl-3-methylimidazolium hexafluorophosphate.

12. A process as specified in claim 2 wherein the ionic liquid has a melting point of less than about 100° C.

13. A process as specified in claim 2 wherein the ionic liquid has a melting point of less than about 50° C.

14. A process as specified in claim 2 wherein the ionic liquid has a melting point of less than about 20° C.

15. A process as specified in claim 3 wherein the alkyl group contains from 1 to about 12 carbon atoms.

16. A process as specified in claim 3 wherein the alkyl group is selected from the group consisting of methyl groups, ethyl groups, normal propyl groups, isopropyl groups, normal butyl groups, isobutyl groups, and tertiary butyl groups.

17. A process as specified in claim 4 wherein the aryl group is selected from the group consisting of naphthyl groups, indenyl groups, anthracyl groups, and phenanthryl groups.

18. A process as specified in claim 2 wherein the epoxide is 1,2-epoxyhexane.

19. A process as specified in claim 1 wherein the epoxide is selected from the group consisting of monofunctionalized epoxides, difunctionalized epoxides, and trifunctionalized epoxides.

20. A process as specified in claim 1 wherein the epoxide is selected from the group consisting of 1,2-epoxy-5-hexane, 1,2-epoxy-3-methylbutane, 1,2-epoxy-2-methylpropane, 1,2-epoxy-7-octene, 1,2-epoxypentane, 1,2-epoxy-3-phenoxypropane, 3,4-epoxy-2-phenyl-1,1,1-trifluoro-2-butanol, (2,3-epoxypropyl)benzene, N-(2,3-epoxypropyl)phthalimide, 3,4-epoxytetrahydrothiophene-1,1-dioxide, glycerol diglycidyl ether, glycerol propoxylate triglycidyl ether, 3-glycidoxypropyldimethoxymethylsilane, 3-glycidoxypropyldimethethoxysilane, (glycidoxypropyldimethylsilyloxy) hepatcyclopentylpentacyclooctasiloxane, 3-glycidoxypropyltrimethoxysilane, (R)-(-)gylcidyl butyrate, glycidyl 2,2,3,3,4,4,5,5,6,6,7,7-dodecafluoroheptyl ether, glycidyl 2,2,3,3,4,4,5,5,6,6,7,7,8,8,9,9-hexadecafluorononyl ether, glycidyl isopropyl ether, glycidyl methacrylate, glycidyl 4-methoxyphenyl ether, (R)-(-)-glycidyl methyl ether, (S)-(-)-glycidyl methyl ether, and (2R)-(-)-glycidyl 3-nitrobenzenesulfonate.

* * * * *